US009399780B2

(12) United States Patent
Shinmura et al.

(10) Patent No.: US 9,399,780 B2
(45) Date of Patent: Jul. 26, 2016

(54) METHOD FOR PRODUCING VIRAL VECTOR

(71) Applicant: TAKARA BIO INC., Shiga (JP)

(72) Inventors: Kazuhisa Shinmura, Shiga (JP); Hirofumi Yoshioka, Shiga (JP); Hikaru Takakura, Shiga (JP); Junichi Mineno, Shiga (JP)

(73) Assignee: TAKARA BIO INC., Shiga (JP)

( * ) Notice: Subject to any disclaimer, the term of this patent is extended or adjusted under 35 U.S.C. 154(b) by 0 days.

(21) Appl. No.: 14/381,721

(22) PCT Filed: Mar. 14, 2013

(86) PCT No.: PCT/JP2013/057184
§ 371 (c)(1),
(2) Date: Aug. 28, 2014

(87) PCT Pub. No.: WO2013/141133
PCT Pub. Date: Sep. 26, 2013

(65) Prior Publication Data
US 2015/0079050 A1 Mar. 19, 2015

(30) Foreign Application Priority Data
Mar. 22, 2012 (JP) .................................. 2012-065857

(51) Int. Cl.
C12N 15/86 (2006.01)
A61K 35/00 (2006.01)
C12N 5/00 (2006.01)
C12N 7/00 (2006.01)
A61K 35/13 (2015.01)
A61K 48/00 (2006.01)

(52) U.S. Cl.
CPC ................ *C12N 15/86* (2013.01); *A61K 35/13* (2013.01); *C12N 5/0018* (2013.01); *C12N 7/00* (2013.01); *A61K 48/00* (2013.01); *C12N 2740/10041* (2013.01); *C12N 2740/10051* (2013.01); *C12N 2740/10052* (2013.01)

(58) Field of Classification Search
None
See application file for complete search history.

(56) References Cited

U.S. PATENT DOCUMENTS

| 5,278,056 | A | 1/1994 | Bank et al. |
| 5,470,726 | A | 11/1995 | Miller et al. |
| 6,787,359 | B1 | 9/2004 | Ueno et al. |
| 7,485,448 | B2 | 2/2009 | Yoshioka et al. |
| 2002/0183388 | A1 | 12/2002 | Gudas et al. |
| 2004/0058447 | A1 | 3/2004 | Ueno et al. |
| 2005/0064594 | A1 | 3/2005 | Gripon et al. |
| 2005/0201983 | A1 | 9/2005 | Yla-Herttuala et al. |
| 2008/0286239 | A1 | 11/2008 | Nielsen et al. |
| 2010/0113566 | A1 | 5/2010 | Chono et al. |
| 2010/0137415 | A1 | 6/2010 | Chono et al. |
| 2010/0273213 | A1 | 10/2010 | Mineno et al. |
| 2013/0183719 | A1 | 7/2013 | Shinmura et al. |

FOREIGN PATENT DOCUMENTS

| JP | 2004-535809 | 12/2004 |
| JP | 2007-105033 | 4/2007 |
| JP | 2011-520470 | 7/2011 |
| JP | 2011-526786 | 10/2011 |
| WO | 92/07943 | 5/1992 |
| WO | 00/01836 | 1/2000 |
| WO | 00/23567 | 4/2000 |
| WO | 01/96532 | 12/2001 |
| WO | 2007/020873 | 2/2007 |
| WO | 2008/133137 | 11/2008 |
| WO | 2009/048024 | 4/2009 |
| WO | 2009/143353 | 11/2009 |
| WO | 2010/002846 | 1/2010 |
| WO | 2012/046727 | 4/2012 |

OTHER PUBLICATIONS

Du, et al. (1999) "Overexpression of Wild-Type Retinoic Acid Receptor α (RARα) Recapitulates Retinoic Acid-Sensitive Transformation of Primary Myeloid Progenitors by Acute Promyelocytic Leukemia RARα-Fusion Genes", Blood, 94(2): 793-802.*
Soneoka, et al. (1996) "A transient three-plasmid expression system for the production of high titer retroviral vectors", Nucleic Acids Research, 23(4): 628-33.*
Kiefer, et al. (2004) "Retinoic Acid Inhibition of Chromatin Remodeling at the Human Immunodeficiency Virus Type I Promoter", The Journal of Biological Chemistry, 279(42): 43604-43613.*
Gaetano, et al. (2000) "Transcriptionally active drugs improve adenovirus vector performance in vitro and in vivo", Gene Therapy, 7: 1624-30.*
Green, et al. (2008) :"Antiaging Effects of Topical Lactobionic Acid: Results of a Controlled Usage Study", Cosmetic Dermatology, 21(2): 76-82.*
International Preliminary Report on Patentability issued Sep. 23, 2014 in International (PCT) Application No. PCT/JP2013/057184.
Tsao et al., "Development and improvement of a serum-free suspension process for the production of recombinant adenoviral vectors using HEK293 cells", Cytotechnology, vol. 37, 2001, pp. 189-198.
Tobias et al., "Improved Recombinant Retroviral Titers Utilizing Trichostatin A", BioTechniques, vol. 29, No. 4, 2000, pp. 884-890.
Olsen et al., "Use of Sodium Butyrate to Enhance Production of Retroviral Vectors Expressing CFTR cDNA", Human Gene Therapy, vol. 6, 1995, pp. 1195-1202.

(Continued)

Primary Examiner — Robert M Kelly
(74) Attorney, Agent, or Firm — Wenderoth, Lind & Ponack, L.L.P.

(57) ABSTRACT

The present invention provides a method for producing a virus vector, which involves a step of culturing a cell capable of producing the virus vector in a culture medium containing a retinoic acid compound, a histone deacetylase-inhibiting substance and a substance capable of forming a chelate; and a culture medium for use in the production of a virus vector, which is characterized by containing a retinoic acid compound, a histone deacetylase-inhibiting substance and a substance capable of forming a chelate as active ingredients.

3 Claims, 2 Drawing Sheets

(56) References Cited

OTHER PUBLICATIONS

Parente et al., "Production of increased titer retovirus vectors from stable producer cell lines by superinfection and concentration", Gene Therapy, vol. 3, 1996, pp. 756-760.
International Search Report issued May 28, 2013 in International (PCT) Application No. PCT/JP2013/057184.
Office Action issued May 28, 2014 in Chinese Application No. 201180048256.4, with English translation.
Gang et al., "Enhancive Effect of Histone Deacetylase Inhibitor Trichostatin A on Transfection Efficiency of Adenovirus in Ovarian Carcinoma Cell Line A2780", Chinese Journal of Cancer, 2005, vol. 24, No. 10, pp. 1196-1200.
Boyko et al., "Coassembly and Complementation of Gag Proteins from HIV-1 and HIV-2, Two Distinct Human Pathogens", Molecular Cell, 23, 281-287, Jul. 21, 2006.
Eck et al., Goodman and Gilman's The Pharmacological Basis of Therapeutics, 1996, pp. 77-101.
Chinese Office Action issued Dec. 4, 2013 in Chinese Application No. 201180048256.4 (with English translation).
Hanai et al., "Endostatin Causes G1 Arrest of Endothelial Cells through Inhibition of Cyclin D1", JBC 1. 277, 16464-16469.
Arts et al., "Stimulation of Tissue-Type Plasminogen Activator Gene Expression by Sodium Butyrate and Trichostatin A in Human Endothelial Cells Involves Histone Acetylation", Biochem. J. (1995), 310, 171-176.
Yasufumi Kaneda, "Vector Development for Cancer Gene Therapy", Biotherapy, vol. 20, No. 3, May 2006, pp. 261-269, with partial English translation.
International Search Report issued Nov. 8, 2011 in International Application No. PCT/JP2011/072871.
Supplementary European Search Report issued Jun. 5, 2013 in corresponding European Patent Application No. 11830659.6.
International Preliminary Report on Patentability and Written Opinion issued May 8, 2013 in International Application No. PCT/JP2011/072871.
Meier, Jeffery L., "Reactivation of the Human Cytomegalovirus Major Immediate-Early Regulatory Region and Viral Replication in Embryonal NTera2 Cells: Role of Trichostatin A, Retinoic Acid, and Deletion of the 21-Base-Pair Repeats and Modulator", Journal of Virology, Feb. 2001, vol. 75, No. 4, pp. 1581-1593.
Faluhelyi et al., "All-trans Retinoic Acid (ATRA) Suppresses Transcription of Human Papillomavirus Type 16 (HPV16) in a Dose-dependent Manner", Anticancer Research, 2004, vol. 24, pp. 807-810.
Nakashima, Hideki, "Inhibitory Effect of Retinoic Acid on Human Immuno-deficiency Virus (HIV) Infection and Replication in vitro", Vitamins (Japan), 1986, vol. 60, No. 11, pp. 527-535.
Caselli et al., "Retinoic Acid Analogues Inhibit Human Herpesvirus 8 Replication", Antiviral Therapy, 2008, vol. 3, pp. 199-209.
Morgenstern et al., "Advanced Mammalian Gene Transfer: High Titre Retroviral Vectors with Multiple Drug Selection Markers and a Complementary Helper-Free Packaging Cell Line", Nucleic Acids Research, 1990, vol. 18, No. 12, pp. 3587-3596.
Danos et al., "Safe and Efficient Generation of Recombinant Retroviruses with Amphotropic and Ecotropic Host Ranges", Proc. Natl. Acad. Sci. USA, Sep. 1988, vol. 85, pp. 6460-6464.
Supplementary European Search Report issued Oct. 6, 2015 in corresponding European Patent Application No. 13763874.8.
Jaalouk et al., "Inhibition of histone deacetylation in 293GPG packaging cell line improves the production of self-inactivating MLV-derived retroviral vectors", Virology Journal, Apr. 2006, vol. 3, No. 27, pp. 1-12.
Brian L. Ellis et al., "Creating Higher Titer Lentivirus with Caffeine", Human Gene Therapy, vol. 22, 2011, pp. 93-100.
U.S. Office Action issued Nov. 20, 2013 in corresponding U.S. Appl. No. 13/823,805.
U.S. Office Action issued Mar. 13, 2014 in corresponding U.S. Appl. No. 13/823,805.
U.S. Office Action issued Feb. 26, 2015 in corresponding U.S. Appl. No. 13/823,805.
U.S. Office Action issued Aug. 6, 2013 in corresponding U.S. Appl. No. 13/823,805.
Extended European Search report issued Jan. 27, 2016 in corresponding European Patent Application No. 13763874.8.

\* cited by examiner

METHOD FOR PRODUCING VIRAL VECTOR

TECHNICAL FIELD

The present invention relates to a method of producing a virus vector and a culture medium for production of a virus vector.

BACKGROUND ART

Gene therapy using a virus vector has been developed for the purposes of treating cancer and infection disease as well as congenital genetic disease, and many clinical trials have been conducted. In particular, many attempts for gene therapy using a retrovirus vector or an adenovirus vector have been made.

Examples of a transfer vector used for producing a recombinant retrovirus vector used for integration of a desired gene include pLXSN (Genbank Accession M28248) and pMFG which are derived from the wild-type Moloney murine leukemia virus (MoMLV) wherein viral particle-structural protein genes (gag, pol, env) are removed from the genome. In addition, a further modified vector is used in clinical trials for human.

A recombinant retrovirus vector is produced by transfecting a packaging cell (Psi-Crip, GP+E86, GP+envAm12, PG13, etc.) with a DNA vector in which a desired gene is inserted to induce a virus producer cell, culturing the virus producer cell, and then harvesting a supernatant containing the desired virus vector. Then, a packaging cell may be infected again with the supernatant, and from among the infected cells, a clone of a producer cell that can stably produce a retrovirus vector for expression of the desired gene may be selected. Through such a process, a master cell bank (MCB) and then a working cell bank (WCB) are prepared, and therefrom a recombinant retrovirus vector for gene therapy is stably produced.

Culture of a retrovirus producer cell is very important for increasing the titer of a virus produced from the retrovirus producer cell. In other words, it is required to examine culture conditions for attaining higher viral titer. Methods of increasing viral titer so far as known involve multiple infection (for example, Non-Patent Literature 1), or addition of sodium butyrate or trichostatin A which is a histone deacetylase inhibitor (for example, Non-Patent Literatures 2 and 3). However, these known methods do not produce remarkable effects.

CITATION LIST

Non-Patent Literature

Non-Patent Literature 1: J. Hum. Gene Ther., Vol. 6, pp. 1195-1202 (1995)
Non-Patent Literature 2: Gene Therapy, Vol. 3, pp. 756-760 (1996)
Non-Patent Literature 3: BioTechniques, Vol. 29, pp. 884-890 (2000)

SUMMARY OF INVENTION

Technical Problems

Objectives of the present invention are to develop a culture medium used for production of a virus vector, in particular, a culture medium used for culture of a virus producer cell that can maintain higher viral titer, and provide a method of producing a virus vector which comprises using the culture medium and a method of producing a transduced cell population which comprises using the virus vector that is produced by the method of producing a virus vector.

Solution to Problems

The present inventors intensively studied to solve the above problems, and as a result, found that enhanced viral production could be continued for a long period and a virus supernatant having surprisingly high viral titer could be obtained when a virus producer cell was cultured using a culture medium containing retinoic acid, a histone deacetylase inhibitor and a substance capable of forming a chelate as active ingredients. Thus the present invention was completed.

Specifically, the present invention relates to:

[1] A method of producing a virus vector, which comprises a step of culturing a cell capable of producing the virus vector in a culture medium containing retinoic acid, a histone deacetylase inhibitor and a substance capable of forming a chelate as active ingredients;

[2] The method according to [1], wherein the cell is a cell capable of producing the virus vector continuously;

[3] The method according to [1] or [2], wherein the virus vector is a retrovirus vector;

[4] The method according to any one of [1] to [3], wherein the histone deacetylase inhibitor is at least one substance selected from the group consisting of trichostatin A and sodium butyrate;

[5] The method according to any one of [1] to [4], wherein the substance capable of forming a chelate is lactobionic acid or a salt thereof;

[6] A method of producing a transduced cell population, which comprises:
    (1) a step of producing a virus vector by the method according to any one of [1] to [5], and
    (2) a step of transducing a cell with the virus vector produced by step (1);

[7] A transduced cell population obtained by the method according to [6];

[8] The cell population according to [7] for use as a medicament;

[9] The cell population according to [7] for use in production of a medicament;

[10] A pharmaceutical composition containing the cell population according to [7] as an active ingredient;

[11] A method of treating or preventing a disease, which comprises administering an effective amount of the pharmaceutical composition according to [10] to a subject; and

[12] A culture medium for production of a virus vector, containing retinoic acid, a histone deacetylase inhibitor and a substance capable of forming a chelate as active ingredients.

Effects of Invention

Since a virus supernatant having high viral titer can be easily obtained by using the culture medium of the present invention, a virus vector and a high titer composition containing the virus vector can be easily prepared. The virus vector and the composition obtained by using the culture medium of the present invention are very useful in the field of gene therapy.

MODE FOR CARRYING OUT THE INVENTION

Figure 1:
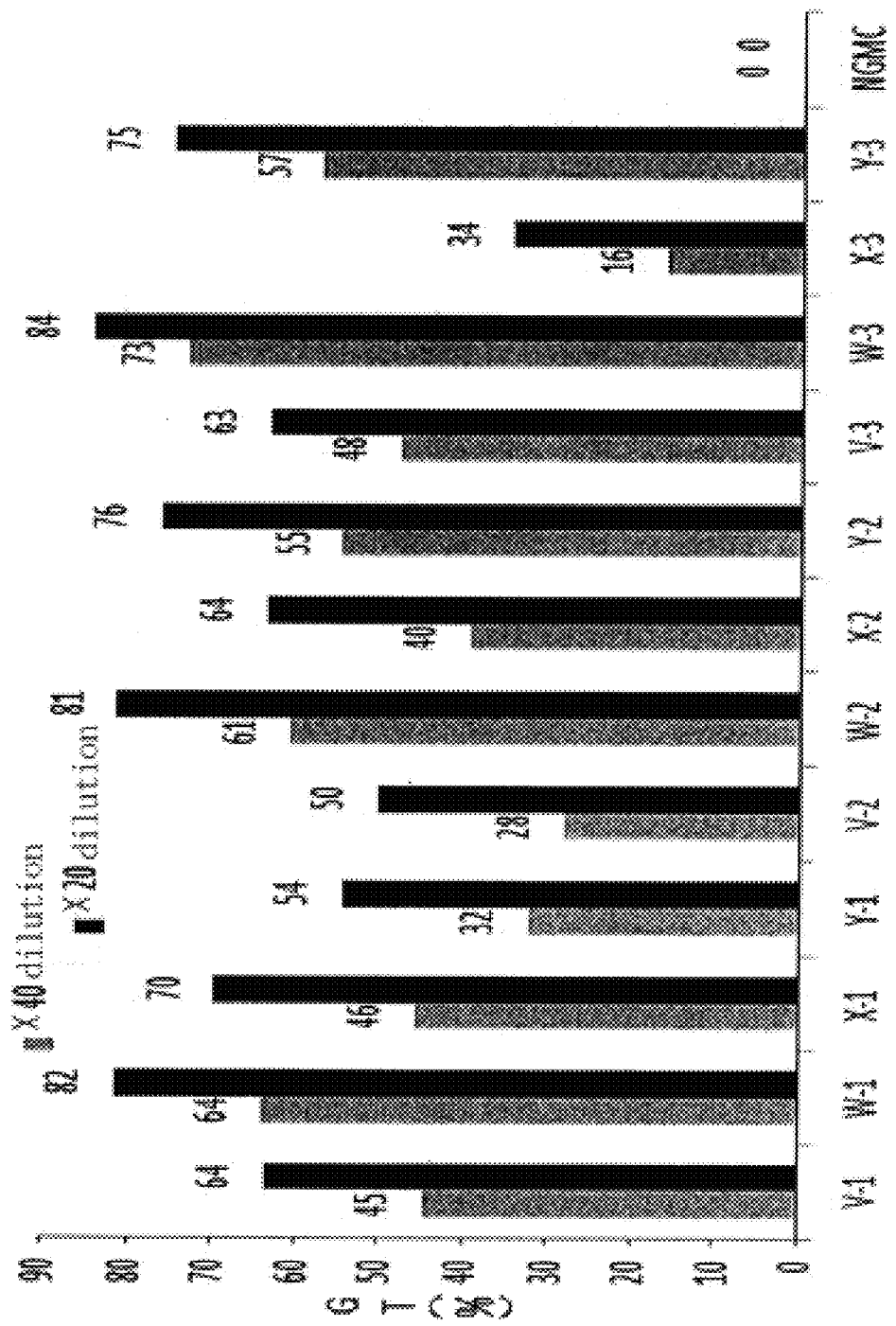
FIG. 1 shows gene transduction efficiency in CCRF-CEM cells with retrovirus vectors obtained using culture media V-1 to V-3, W-1 to W-3, X-1 to X-3, Y-1 to Y-3, etc.

Hereinafter, the present invention is explained in detail.

The present invention discloses a culture medium suitable for culture of a cell producing a virus vector. The culture medium comprises a basal medium which is prepared by mixing necessary ingredients for cell culture and further contains retinoic acid and a histone deacetylase inhibitor and a substance capable of forming a chelate as active ingredients. The culture medium may further contain lipid.

In the present invention, the "retinoic acid" is also called vitamin A acid, and may be either all-trans-retinoic acid, in which all double bonds on the chain part are in the trans form, or 9-cis-retinoic acid, in which a double bond at the 9-position is in the cis form. Other retinoic acid isomers, retinoic acid derivatives, and synthetic retinoids that are artificially synthesized can be also used in the present invention. As used herein, the above-described retinoic acids, retinoic acid isomers, retinoic acid derivatives, synthetic retinoids that are artificially synthesized, and their salts are collectively referred to as retinoic acid. The retinoic acid used in the present invention may be one kind of retinoic acid or a combination of plural kinds of retinoic acid.

The concentration of the retinoic acid used in the present invention in the culture medium is not particularly limited as long as it is such a concentration that the retinoic acid behaves as the active ingredient. When all-trans-retinoic acid (hereinafter, referred to as ATRA) is used, the concentration is, for example, preferably 1 nM to 10 µM, more preferably 5 nM to 200 nM, still more preferably 10 nM to 100 nM.

In the present invention, the "histone deacetylase inhibitor" may be any substance having histone deacetylase activity. Examples of the histone deacetylase inhibitor that can be used in the present invention include (1) fatty acids, such as sodium butyrate, butyrate, phenyl butyrate, valproic acid, and their salts, derivatives, and the like (2) hydroxamic acids, such as trichostatin A, oxamflatin, suberoylanilide, and their salts, derivatives, and the like, (3) cyclic peptides, such as trapoxin, apicidin, FK228, and their salts, derivatives, and the like, and (4) benzamide, and its salts, derivatives, and the like. Furthermore, the histone deacetylase inhibitor used in the present invention may be one kind of histone deacetylase inhibitor or a combination of plural kinds of histone deacetylase inhibitors.

Preferred examples of the histone deacetylase inhibitor include, but not limited to, sodium butyrate (hereinafter, referred to as NaB), and trichostatin A (hereinafter, referred to as TSA) which can inhibit a broad range of isoforms of histone deacetylases. The present inventors have found that not only NaB but also TSA produces a synergistic effect when the histone deacetylase inhibitor is used in combination with retinoic acid.

The concentration of the histone deacetylase inhibitor used in the present invention in the culture medium is not particularly limited as long as it is such a concentration that the histone deacetylase inhibitor behaves as the active ingredient. When TSA is used, the concentration is, for example, preferably 10 nM to 50 µM, more preferably 20 nM to 10 µM, still more preferably 100 nM to 3 µM. When NaB is used, the concentration is, for example, preferably 1 nM to 50 mM, more preferably 1 mM to 10 mM.

The culture medium containing retinoic acid and a histone deacetylase inhibitor of the present invention may further contain lipid. Examples of the lipid that can be used in the present invention include fatty acids (arachidonic acid, linoleic acid, linolenic acid, myristic acid, oleic acid, palmitoylic acid, palmitic acid, and their salts, and the like); steroids such as cholesterols, and dexamethasones; tocopherol acetate; triglycerides; and phospholipids (glycerophospholipid, sphingophospholipid, inositolphospholipid, and the like). One kind or a combination of plural kinds of the lipid as described above may be added to the culture medium. For example, the culture medium may contain a fatty acid concentrate as it is, which is commercially available as a medium additive to substitute for serum components.

The concentration in the culture medium of any lipid selected from the above-described lipids that can be used in the present invention is not particularly limited as long as it is such a concentration that the lipid behaves as the active ingredient. The total lipid concentration in the culture medium is preferably 0.01 mg/L to 8.0 mg/L, more preferably 0.03 mg/L to 5.0 mg/L, still more preferably 0.1 mg/L to 4.0 mg/L. For example, when the fatty acid concentrate is used, the concentration in terms of a volume ratio is preferably 1/10,000 to 1/50 (V/V), more preferably 1/3,000 to 1/75 (V/V), still more preferably 1/1,000 to 1/100 (V/V).

In the present invention, the "substance capable of forming a chelate" may be any substance that can coordinate to a metal ion to form a complex. Examples of the substance capable of forming a chelate that can be used in the present invention include EDTA (ethylenediaminetetraacetic acid) NTA (nitrilotriacetic acid), DTPA (diethylenetriaminepentaacetic acid), HEDTA (hydroxyethylenediamine triacetic acid) and the like, as aminocarboxylate chelators; HEDP (hydroxyethylidenephosphonic acid), NTMP [nitrilotris(methylenephosphonic acid)], EDTMP [ethylenediamine tetra(methylenephosphonic acid)] and the like, as phosphonate chelators; bipyridine, phenanthroline, porphyrin, crown ether, cyclam, terpyridine, catecholate, BINAP [2,2'-bis(diphenylphosphino)-1,1'-binaphthyl] and the like, as other ligands; and lactobionic acid, gluconic acid, inositol hexaphosphate, citric acid, phosphoric acid, malic acid, mugineic acid, glutathione, alpha lipoic acid, L-carnitine, L-methionine, L-cystine, MSM (methylsulfonylmethane) and the like, as other substances. Also, salts of the above-described substances can be used. Furthermore, the substance capable of forming a chelate that is used in the present invention may be one kind of substance or a combination of plural kinds of substances.

Preferred examples of the substance capable of forming a chelate include, but not limited to, lactobionic acid and a salt thereof (for example, calcium lactobionate).

The concentration of the substance capable of forming a chelate that is used in the present invention in the culture medium is not particularly limited as long as it is such a concentration that the substance capable of forming a chelate behaves as the active ingredient. When calcium lactobionate is used, the concentration is, for example, preferably a final concentration of 2 µM to 200 mM, more preferably a final concentration of 20 µM to 20 mM, still more preferably a final concentration of 200 µM to 2 mM.

Examples of the ingredients of the basal medium include energy sources such as amino acids, saccharides and organic acids, vitamins, buffering ingredients for pH adjustment, and inorganic salts. The basal medium may also contain a pH indicator such as phenol red. Examples of the basal medium that may be used include known serum-free culture media, such as DMEM, IMDM, and Ham's F12 medium which are commercially available from Invitrogen, Sigma, and the like.

Commercially available culture media such as Opti-ProSFM, VP-SFM, 293SFMII (which are manufactured by Invitrogen), and HyQ SFM4MegaVir (manufactured by HyClone Laboratories Inc) can be also used. Although a serum-supplemented culture medium may be used as the basal medium, a serum-free culture medium is preferably used in order to prevent contamination with serum-derived unknown viruses. When a serum-free culture medium is used, a serum-free culture medium containing serum albumin highly purified from human blood (e.g., a serum albumin preparation approved as a drug), highly purified serum albumin derived from an animal, or recombinant serum albumin is preferably used (JP-A 2007-105033).

A virus producer cell to be cultured in the culture medium of the present invention is not particularly limited, and for example, preferred is a retrovirus producer cell.

The present invention relates to a method of producing a virus vector which comprises using the culture medium as described above.

The virus vector that can be produced according to the present invention is not particularly limited. Examples of the virus vector include retrovirus vectors (including oncovirus vectors, lentivirus vectors, and their modified forms), adenovirus vectors, adeno-associated virus vectors, simian virus vectors, vaccinia virus vectors, and sendaivirus vectors. Preferred examples of the virus vector include retrovirus vectors and recombinant retrovirus vectors. Particularly, a retrovirus vector lacking the replication ability so as to prevent unlimited infection or gene transfer is preferably used in the present invention. A nucleic acid to be enclosed within the viral particle of a recombinant retrovirus vector is usually provided by a plasmid. Examples of known plasmids for providing a nucleic acid to be enclosed within the viral particle of a retrovirus vector lacking the replication ability include retrovirus vector plasmids such as a MFG vector, an α-SGC vector (WO92/07943), pBabe [Nucleic Acids Research, vol. 18, pp. 3587-3596 (1990)], pLXIN (manufactured by Clontech), and pDON-AI (manufactured by TAKARA BIO INC.), lentivirus vectors [human immunodeficiency virus (HIV)-derived vectors, simian immunodeficiency virus (SIV)-derived vectors, etc.], and vector plasmids obtained by modifying them.

The nucleic acid to be enclosed within the viral particle may contain any foreign gene. The foreign gene is not particularly limited, and any gene [a gene encoding protein such as an enzyme, a cytokine, or a receptor, as well as a gene encoding an intracellular antibody, an antisense nucleic acid, an siRNA (small interfering RNA), or ribozyme] can be used depending on the intended uses of a cell population transduced with the virus vector produced according to the present invention as described below. Examples of the foreign gene include, for the purpose of medical use of cells, a gene for expressing MazF which is a sequence-specific ribonuclease (e.g., WO 2007/020873 and WO 2008/133137), a gene encoding an antibody variable region that recognizes a tumor antigen or a viral antigen, or a T cell receptor, and a gene which is lacked or whose function is lost in a patient. At the same time, the nucleic acid to be enclosed within the viral particle may contain a suitable marker gene that allows for selection of a gene-transduced cell, such as an extracellular domain gene of a low affinity nerve growth factor receptor (ΔLNGFR), a neomycin-resistant gene, or a fluorescent protein gene.

For example, the foreign gene can be loaded into the virus vector in such a manner that the gene is expressed under the control of a suitable promoter. An enhancer sequence, a terminator sequence, or an intron sequence may be also present in the vector.

In the present invention, the production of the retrovirus vector is carried out by transfecting a DNA for providing the nucleic acid to be enclosed within the viral particle of the retrovirus vector into a retrovirus packaging cell line to prepare a retrovirus producer cell, and culturing the retrovirus producer cell in the culture medium of the present invention.

The packaging cell line is not particularly limited, and a known packaging cell line, such as PG13 (ATCC CRL-10686), PA317 (ATCC CRL-9078), GP+E-86 or GP+envAm-12 (U.S. Pat. No. 5,278,056), or Psi-Crip [Proc. Natl. Acad. Sci. USA, vol. 85, pp. 6460-6464 (1988)] can be used. A packaging plasmid carrying genes necessary for production of retroviral particles (Retrovirus Packaging Kit manufactured by TAKARA BIO INC., etc.) can be also transfected into a 293 cell or a 293 T cell having a high transfection efficiency to prepare packaging cells.

The method of the present invention can be applied to either a virus producer cell line prepared so as to transiently produce a recombinant virus vector, or a virus producer cell line capable of continuously producing a virus. In the case where the latter virus producer cell line is used, a frozen stock of the virus producer cell line such as a master cell bank (MCB) or a working cell bank (WCB) is thawed by a suitable means, and then directly seeded in the culture medium to start the culture, and the cell is grown to allow the cell to produce the virus. For preparation of a recombinant virus vector in large scale, it is preferable that an acclimation step for adapting the virus producer cell line to the culture medium is further added.

The virus producer cell can be cultured under conventional culture conditions. Examples of the culture conditions include, but not limited to, culture at 95% of humidity and 5% $CO_2$. The culture of the virus producer cell can be carried out, for example at 30 to 37° C. However, the culture of the virus producer cell may be carried out at a temperature falling outside the above-described range as long as it is such a temperature that the growth of the desired cell and the production of the virus vector can be attained. In the present invention, production of a retrovirus vector is carried out by harvesting a supernatant from the culture solution thus obtained. The virus vector may be the above-described supernatant as it is, or a filtrate obtained by filtering the supernatant, or may be concentrated or purified by a known method. The virus vector is kept by a suitable means, for example by freezing, until use. By the culture of the virus producer cell in the culture medium of the present invention as described above, a virus vector with higher titer can be obtained as compared with a conventional culture method.

The present invention also provides a method of producing a cell population containing transduced cells which comprises transducing a target cell with the virus vector produced by the method of the present invention. The number of the desired genes to be transduced into a cell by the virus vector is not limited. One gene or two or more genes may be transduced by the virus vector. The transduction of the target cell with the virus vector may be carried out by a known method suitable for the virus vector. For example, when a retrovirus vector is used, a substance capable of enhancing gene transduction efficiency such as RetroNectin (registered trademark; manufactured by TAKARA BIO INC.) can be also used at the time of carrying out gene transduction.

Since a virus vector with high viral titer can be obtained according to the present invention, a cell population comprising a high percentage of cells retaining a desired gene can be obtained by using the virus vector.

The present invention provides a cell population obtained by the method of producing a cell population of the present invention, and use of the cell population. The cell population obtained by the method of the present invention can be used for various purposes, for example for production of useful substances. The cell population itself can be also used for treatment of disease.

According to the method of the present invention, a cell population containing cells retaining a therapeutically useful foreign gene can be obtained. The cell population can be used for treatment of various diseases, such as cancer, leukemia, malignant tumors, hepatitis, infectious diseases [e.g., influenza, tuberculosis, HIV (Human Immunodeficiency virus) infection, AIDS, MRSA infection, VRE infection, and deep mycosis], and the like. The cell population produced by the method of the present invention can be also utilized in combination with a conventional therapeutic method, such as donor lymphocyte infusion for the purpose of prevention of infectious disease in an immunodeficiency state after bone marrow transplantation, exposure to radiation, or the like, or remission of relapsed leukemia, anticancer drug therapy, radiation therapy, antibody therapy, thermotherapy, or other immunotherapy.

When the cell population containing transduced cells obtained according to the present invention is used for treatment or prevention of disease, an effective amount of the cell is administered to a subject for the treatment or prevention, that is, a human or a non-human animal. A method of administration of the cell population may be selected appropriately depending on the disease. Examples of the administration method include intravenous administration, intraarterial administration, subcutaneous administration, and intraperitoneal administration, by injection or infusion.

The cell population obtained according to the present invention can be formulated into a pharmaceutical composition, that is, a therapeutic agent or a preventive agent for disease. The pharmaceutical composition can be formulated can be produced by formulating the cell population according to a method known in the pharmaceutical filed. For example, the cell population produced by the method of the present invention as the active ingredient can be mixed with a known organic or inorganic carrier, excipient or stabilizer which is suitable for parenteral administration, or the like to prepare an infusion or an injection.

EXAMPLES

Hereinafter, the present invention is further specifically explained by means of Examples to which the present invention is not limited.

Example 1

Preparation of Calcium Lactobionate Monohydrate (LaCa) (Manufactured by Sigma)-Supplemented Culture Medium 1

DMEM medium (manufactured by Gibco) containing inactivated fetal bovine serum (FBS, manufactured by SAFC Bioscience) at the solution ratio (V/V) of 1/10 was used as the basal medium (culture medium V). To culture medium V was added LaCa to prepare culture media V-1 (final concentration: 20 μM), V-2 (final concentration: 200 μM), and V-3 (final concentration: 2 mM). Furthermore, to each of culture media V-1, V-2 and V-3 were added retinoic acid (ATRA) (manufactured by Wako Pure Chemical Industries, Ltd.) at a final concentration of 100 nM and sodium butyrate (NaB) (manufactured by Wako Pure Chemical Industries, Ltd.) at a final concentration of 5 mM to prepare culture media W-1, W-2 and W-3 respectively. As a comparative group, to each of culture media V-1, V-2 and V-3 was added only NaB (final concentration: 5 mM) to prepare culture media X-1, X-2 and X-3 respectively, and was added only ATRA (final concentration: 100 nM) to prepare culture media Y-1, Y-2 and Y-3 respectively. The composition of each culture medium is shown in Table 1.

TABLE 1

| Culture medium | LaCa | ATRA | NaB |
|---|---|---|---|
| V-1 | 20 μM | — | — |
| V-2 | 200 μM | | |
| V-3 | 2 mM | | |
| W-1 | 20 μM | 100 nM | 5 mM |
| W-2 | 200 μM | | |
| W-3 | 2 mM | | |
| X-1 | 20 μM | — | 5 mM |
| X-2 | 200 μM | | |
| X-3 | 2 mM | | |
| Y-1 | 20 μM | 100 nM | — |
| Y-2 | 200 μM | | |
| Y-3 | 2 mM | | |

Example 2

Culture of Retrovirus Producer Cell 1

1. Culture of Retrovirus Producer Cell

A working cell bank (WCB) of a retrovirus producer cell capable of producing a mouse-derived recombinant retrovirus vector carrying a fluorescent reporter protein (ZsGreen) gene (PG13: ATCC CRL-10686 was used as a packaging cell) was thawed in a water bath at 37° C. The cell solution thus thawed was put into a 15 mL centrifuging tube. After addition of 10 mL of a complete medium (a DMEM medium containing 10% PBS), the tube was subjected to centrifugation (500× g, 5 minutes, 20° C.). After the centrifugation, a supernatant was removed, and the cells were suspended in 10 mL of the complete medium and then counted. After cell counting, the cell suspension was adjusted with the complete medium to $78.5 \times 10^4$ cells/mL. To a 100 mm dish for cell culture (manufactured by IWAKI) were added 1 mL of the cell suspension and 14.7 mL of the complete medium. The cell culture was carried out in a $CO_2$ incubator (37° C., 95% of humidity, 5% $CO_2$). The cell was subcultured at intervals of 3 days. At the 1st passage, the cell suspension was seeded at the cell density of $1 \times 10^4$ cells/cm$^2$ and the volume of 0.2 mL/cm$^2$. At the 2nd passage, 2 mL/well of the cell suspension was seeded at the cell density of $0.9 \times 10^4$ cells/cm$^2$ and the volume of 0.2 mL/cm$^2$ onto a 6-well treated plate for cell culture (manufactured by BD Falcon). Three days after the start of culture at the 2nd passage, a culture supernatant was removed and replaced with culture medium V-1, V-2, V-3, W-1, W-2, W-3, Y-1, Y-2, or Y-3 as described in Example 1 (volume: 0.1 mL/cm$^2$). On the following day, the culture medium was collected and replaced with a fresh culture medium that was of the same kind as that of the collected culture medium. After lapse of 3 days at the 2nd passage, the cell culture was carried out at 32° C., 95% of humidity and 5% $CO_2$. The collection and replacement of the culture medium were carried out a total of 3 times for consecutive 3 days, provided that for the 3rd time, only the collection of the culture medium was carried out and a fresh culture medium thereof was not added. The collected culture supernatants (the 1st, 2nd, and 3rd times) were mixed and then filtered through a filter with pore size of 0.22 μm (manufactured by Millipore). The filtrate was used as a retrovirus supernatant.

2. Evaluation of Gene Transduction with Retrovirus Supernatant

The gene transduction efficiency of each retrovirus supernatant collected using culture media V-1 to Y-3 as described above was determined. Each of the retrovirus supernatants collected using media V-1 to Y-3 was diluted to prepare 20-fold and 40-fold virus diluted solutions. For the dilution of the retrovirus supernatants, a physiological saline containing 5% by volume of ACD-A (manufactured by Terumo Corporation) and human serum albumin "Albuminar 25%" (manufactured by CSL Behring) at a final albumin concentration of 2% was used. As a vessel for gene transduction, a 24-well nontreated plate (manufactured by BD Falcon) was used. The 24-well nontreated plate was treated at 4° C. overnight with addition of 0.5 mL/well of a solution of RetroNectin (registered trademark, manufactured by TAKARA BIO INC.) which was previously diluted with ACD-A so as to have a final concentration of 20 μg/mL. After the solution of RetroNectin was removed from the plate, the plate was washed 2 times by addition of 0.5 mL of ACD-A to each well and then removal of the ACD-A. To each well of the washed plate was added 1 mL of each virus diluted solution. The plate was subjected to centrifugation (32° C., 2000×g, 2 hours). After centrifugation, a supernatant of the virus diluted solution was removed from each well. Each well was washed 3 times with 0.5 mL of a diluted solution of human serum albumin "Albuminar 25%" which was prepared by addition of a physiological saline so as to have a final albumin concentration of 1.5%. A human T-cell leukemia cell line CCRF-CEM (ATCC CCL-119) was suspended at $1\times10^6$ cells/mL in a medium for culture of CORE-OEM [a RPMI1640 medium (manufactured by Sigma) containing 10% FBS]. To each well of the washed 24-well nontreated plate as described above was added 1 mL of the cell suspension ($0.5\times10^6$ cells/cm$^2$). The plate was subjected to centrifugation (32° C., 1000×g, 10 minutes). After centrifugation, the plate was incubated for 1 day in a $CO_2$ incubator (37° C., 95% of humidity, 5% $CO_2$). On the following day, 1 mL of the medium for culture of CCRF-CEM was added to each well, and the cell culture was continued for another 1 day. After the culture, the expression of ZsGreen was checked to determine the gene transduction efficiency of the retrovirus. Then, $0.5\times10^6$ cells of the infected and cultured cell were put into a 1.5 mL tube, and then precipitated by centrifugation (4° C., 500×g, minutes). After a supernatant was removed, the precipitated cells were suspended in 950 μL of a phosphate buffer (manufactured by Gibco) supplemented with BSA (bovine serum albumin, manufactured by Sigma) at a final concentration of 0.5% (hereinafter, referred to as 0.5% BSA/PBS). Then, the cells were precipitated again by centrifugation (4° C., 500×g, 5 minutes). After a supernatant was removed, the precipitated cells were suspended in 400 μL of 0.5% BSA/PBS. The suspension was subjected to flow cytometry measurement.

3. Flow Cytometry Measurement

Flow cytometry measurement was carried out using a BD FACSCanto II flow cytometer (Becton, Dickinson and Company) according to the instructions attached to the equipment. First, the above-described suspension was provided to the flow cytometer. On a 2-parameter histogram of a forward scattered light (FSC) and a side scattered light (SSC) (x-axis: FSC, y-axis: SSC), a cell population to be measured was gated. Then, ZsGreen fluorescent intensities of cells within the gate were measured and developed with a histogram (x-axis: fluorescence intensity of ZsGreen, y-axis: cell counts). A cell having a higher ZsGreen fluorescence intensity than an isotype control was defined as a ZsGreen-positive cell. The rate (%) of the number of ZsGreen-positive cells relative to the number of cells within the gate (GT %: gene transduction efficiency) and the mean fluorescence intensity (MFI) were calculated by the following equations.

GT %=(the number of ZsGreen-positive cells/the number of cells within a gate)×100

MFI=Mean value of fluorescence intensities of ZsGreen-positive cells

Gene transduction efficiencies are shown in FIG. 1.

As shown in FIG. 1, the gene transduction efficiencies of the retrovirus supernatants collected using culture media W-1, W-2 and W-3 were about 1.5 to 2 times higher than those of the retrovirus supernatants collected using comparative culture media V-1, V-2 and V-3. In other words, this result means that a virus obtained using a culture medium containing the combination of calcium lactobionate, retinoic acid and a histone deacetylase inhibitor exhibits a higher gene transduction efficiency than a virus obtained using a culture medium supplemented with only calcium lactobionate which is capable of forming a chelate. In Figures, "NGMC" means a cell that has not been transduced with a gene, and represents a negative control. Hereinafter, "NGMC" has the same meaning.

Figure 2:
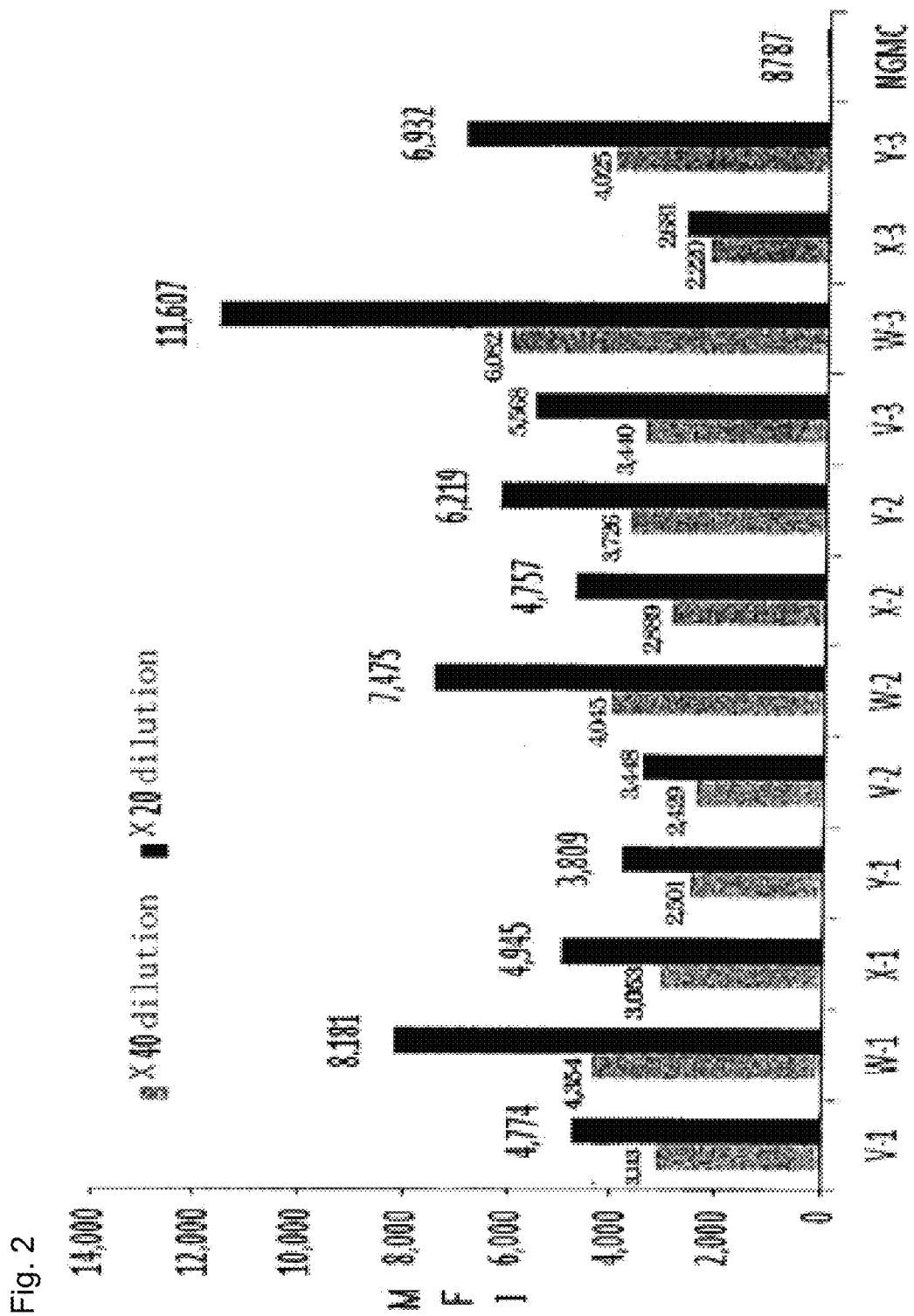
FIG. 2 shows expression intensity of a gene that has been transduced into CCRF-CEM cells with retrovirus vectors obtained using culture media V-1 to V-3, W-1 to W-3, X-1 to X-3, Y-1 to Y-3, etc.

The mean values of fluorescence intensities are shown in FIG. 2.

As shown in FIG. 2, the fluorescence intensities of the cells transduced with the retrovirus supernatants collected using culture media W-1, W-2 and W-3 were about 1.5 to 2 times higher than those of the cells transduced with the retrovirus supernatants collected using culture media V-1, V-2 and V-3. Transduction with the virus obtained using a culture medium containing the combination of calcium lactobionate, retinoic acid and a histone deacetylase inhibitor produced a cell population having a higher ZsGreen fluorescent intensity, as compared with transduction with the virus obtained using a culture medium supplemented with only calcium lactobionate. This result shows a higher gene transduction efficiency, like the above-described result.

Example 3

Preparation of Calcium Lactobionate Monohydrate (LaCa) (Manufactured by Sigma)-Supplemented Culture Medium 2

In the same manner as Example 1, to culture media V-1, V-2 and V-3 were added ATRA at a final concentration of 100 nM and NaB at a final concentration of 5 mM to prepare culture media W-1, W-2 and W-3 respectively. At the same time, culture medium W which was not supplemented with LaCa was prepared. The composition of each culture medium is shown in Table 2.

TABLE 2

| Culture medium | LaCa | ATRA | NaB |
|---|---|---|---|
| W | — | 100 nM | 5 mM |
| W-1 | 20 μM | | |
| W-2 | 200 μM | | |
| W-3 | 2 mM | | |

Example 4

Culture of Retrovirus Producer Cell 2

The four kinds of culture media as prepared in Example 3 were used to prepare retrovirus supernatants in the same manner as Example 2. For each retrovirus supernatant, a gene transduction efficiency and a mean fluorescent intensity were determined.

Gene transduction efficiencies are shown in Table 3.

TABLE 3

| Culture medium | GT % | |
|---|---|---|
| | x40 dilution | x20 dilution |
| W | 35.0 | 62.0 |
| W-1 | 64.0 | 82.0 |
| W-2 | 61.0 | 81.0 |
| W-3 | 73.0 | 84.0 |
| NGMC | 0.0 | |

As shown in Table 3, the gene transduction efficiencies of the retrovirus supernatants collected using culture media W-1, W-2 and W-3 were about 1.5 to 2 times higher than that of the retrovirus supernatant collected using culture medium W which did not contain LaCa. In other words, this result means that when a culture medium containing the combination of retinoic acid and a histone deacetylase inhibitor is supplemented with calcium lactobionate which is capable of forming a chelate, a retrovirus supernatant having a high gene transduction efficiency is obtained by using the culture medium.

The mean values of fluorescence intensities are shown in Table 4.

TABLE 4

| Culture medium | MFI | |
|---|---|---|
| | x40 dilution | x20 dilution |
| W | 2654 | 4520 |
| W-1 | 4354 | 8181 |
| W-2 | 4045 | 7475 |
| W-3 | 6082 | 11607 |
| NGMC | 87 | |

As shown in Table 4, the ZsGreen-derived mean fluorescence intensities of the cells transduced with the retrovirus supernatants collected using culture media W-1, W-2 and W-3 were about 1.6 to 2.6 times higher than that of the cells transduced with the retrovirus supernatant collected using culture medium W which did not contain LaCa. The increased mean fluorescent intensities probably result from increase of the copy number of the ZsGreen gene transduced into the cells. In other words, like the above-described result, this result means that when a culture medium containing the combination of retinoic acid and a histone deacetylase inhibitor is supplemented with LaCa which is capable of forming a chelate, a retrovirus supernatant having a high gene transduction efficiency is obtained by using the culture medium.

Comparative Example

Evaluation of Calcium Lactobionate Monohydrate (LaCa) (Manufactured by Sigma)-Supplemented Culture Medium As described in Example 1, culture medium V was supplemented with only LaCa to prepare culture media V-1 (final concentration: 20 μM), V-2 (final concentration: 200 μM) and V-3 (final concentration: 2 mM). The composition of each culture medium is shown in Table 5.

TABLE 5

| Culture medium | LaCa | ATRA | NaB |
|---|---|---|---|
| V | — | — | — |
| V-1 | 20 μM | | |
| V-2 | 200 μM | | |
| V-3 | 2 mM | | |

These four kinds of culture media were used to prepare retrovirus supernatants in the same manner as Example 2. For each retrovirus supernatant, a gene transduction efficiency and a mean fluorescent intensity of transduced cells were determined.

Gene transduction efficiencies are shown in Table 6.

TABLE 6

| Culture medium | GT % | |
|---|---|---|
| | x40 dilution | x20 dilution |
| V | 44.0 | 66.0 |
| V-1 | 45.0 | 64.0 |
| V-2 | 28.0 | 50.0 |
| V-3 | 48.0 | 63.0 |
| NGMC | 0.0 | |

As shown in Table 6, the gene transduction efficiencies of the retrovirus supernatants collected using culture media V-1, V-2 and V-3 were about the same as that of the retrovirus supernatant collected using culture medium V which did not contain LaCa. In other words, this result means that when a culture medium is supplemented with only LaCa which is capable of forming a chelate (when retinoic acid and a histone deacetylase inhibitor do not coexist with LaCa in a culture medium), the gene transduction efficiency of a retrovirus supernatant obtained by using the culture medium is not increased.

The mean values of fluorescence intensities are shown in Table 7.

TABLE 7

| Culture medium | MFI | |
|---|---|---|
| | x40 dilution | x20 dilution |
| V | 3377 | 5453 |
| V-1 | 3113 | 4774 |
| V-2 | 2420 | 3448 |
| V-3 | 3440 | 5568 |
| NGMC | 87 | |

As shown in Table 7, the ZsGreen-derived mean fluorescence intensities of the cells transduced with the retrovirus supernatants collected using culture media V-1, V-2 and V-3 were about the same as that of the cells transduced with the retrovirus supernatant collected using culture medium V which did not contain LaCa. This result also shows that when a culture medium is supplemented with only LaCa which is capable of forming a chelate, the gene transduction efficiency of a retrovirus supernatant obtained by using the culture medium is not increased.

INDUSTRIAL APPLICABILITY

According to the present invention, a culture medium suitable for culture of cells, in particular, virus producer cells is provided. Using the culture medium of the present invention, viral production can be continued for a longer period than ever before, and thereby high viral titer can be obtained. Therefore, according to the present invention, a large amount of a virus can be collected by one round of culture preparation. Furthermore, according to the present invention, it is possible to increase efficiency of infection to a target cell, etc.

The invention claimed is:

1. A method of producing a retrovirus vector, which comprises:
   a step of culturing a cell producing the retrovirus vector in a culture medium containing retinoic acid, a histone deacetylase inhibitor and a substance forming a chelate as active ingredients, and
   a step of harvesting a supernatant containing the retrovirus vector from the culture medium,
   wherein the substance forming a chelate is lactobionic acid or a salt thereof.

2. The method according to claim 1, wherein the cell continuously produces the retrovirus vector.

3. The method according to claim 1, wherein the histone deacetylase inhibitor is at least one substance selected from the group consisting of trichostatin A and sodium butyrate.

* * * * *